United States Patent [19]

Charbonnier et al.

[11] Patent Number: 5,111,813
[45] Date of Patent: May 12, 1992

[54] DEFIBRILLATION EMPLOYING AN IMPEDANCE-CORRECTED DELIVERED ENERGY

[75] Inventors: Francis M. Charbonnier, McMinnville; Martin G. Rockwell, Sherwood, both of Oreg.

[73] Assignee: Hewlett-Packard Company, Palo Alto, Calif.

[21] Appl. No.: 526,412

[22] Filed: May 18, 1990

[51] Int. Cl.⁵ .............................................. A61N 1/39
[52] U.S. Cl. .................................. 128/419 D; 128/734
[58] Field of Search ............................ 128/419 D, 734

[56] References Cited

U.S. PATENT DOCUMENTS

| | | | |
|---|---|---|---|
| 3,860,009 | 1/1975 | Bell et al. | 128/419 D |
| 3,886,950 | 6/1975 | Ukkestad et al. | 128/419 D |
| 4,077,413 | 3/1978 | Partridge | 128/419 D |
| 4,119,903 | 10/1978 | Pirkle | 128/419 D |
| 4,233,659 | 11/1980 | Pirkle | 128/419 D |
| 4,303,075 | 12/1981 | Heilman et al. | 128/419 D |
| 4,328,808 | 5/1982 | Charbonnier et al. | 128/419 D |
| 4,574,810 | 3/1986 | Lerman | 128/419 D |
| 4,771,781 | 9/1988 | Lerman | 128/419 D |
| 4,840,177 | 6/1989 | Charbonnier et al. | 128/419 D |

OTHER PUBLICATIONS

Schuder et al., "Transthoracic Ventricular Defibrillation in the 100 kg Calf with Untruncated and Truncated Exponential Stimuli", IEEE Transactions on Biomedical Engineering, vol. BME-27, No. 1, Jan. 1980, pp. 37-43.
Kerber et al., "Transthoracic Resistance in Human Defibrillation," Circulation, vol. 63, No. 3, Mar. 81, pp. 676-682.
Lerman et al., "Current-Based Versus Energy-Based Ventricular Defibrillation": A Prospective Study, JACC vol. 12, No. 5, Nov. 1988, pp. 1259-1264.
Kerber, et al., "Energy, Current, and Success in Defibrillation and Cardioversion: Clinical Studies Using an Automated Impedance-Based Method of Energy Adjustment," Circulation, vol. 77, No. 5, May 1988.
Bourland et al., "Strength-Duration Curves for Trapezoidal Waveforsm," Medical Instrumentation, vol. 12, No. 1, Jan.-Feb. 1978, pp. 38-41.
Peleska, "Optimal Parameters of Electrical Impulses for Defibrillation by Consenser Discharges," Circulation, Research, vol. XVIII, Jan. 1966, pp. 10-17.
Bourland, et al., "Comparative Efficacy of Damped Sine Wave and Square Wave Current," Medical Instrumentation, vol. 12, No. 1, Jan.-Feb. 1978, pp. 42-45.
Geddes et al., "Fundamental Criteria Underlying the Efficacy and Safety of Defibrillation Current Waveforms," Med. & Biol. Eng. & Comput., 1985, 23, pp. 122-130.
Koning et al., "Amplitude-Duration Relation for Direct Ventricular Defibrillation With Rectangular Current Pulses," Med. & Biol. Eng., May, 1975, pp. 388-395.
Geddes et al., "Engineering and Physiological Considerations of Direct Capacitor-Discharge Ventricular Defibrillation," Med. & Biol. Eng., vol. 9, 1971, pp. 185-199.

*Primary Examiner*—William E. Kamm
*Assistant Examiner*—Kennedy J. Schaetzle

[57] ABSTRACT

Impedance-normalized delivered energy is used as a control parameter in a defibrillation methodolgy and can be selected to yield the highest probability of successful defibrillation while minimizing the risk of damage to the myocardium and nerve system. This control parameter is essentially independent of patient transthoracic impedance and of discharge pulse waveform and duration, thereby making it advantageous as a standard on which a universal defibrillation protocol may be based.

15 Claims, 5 Drawing Sheets

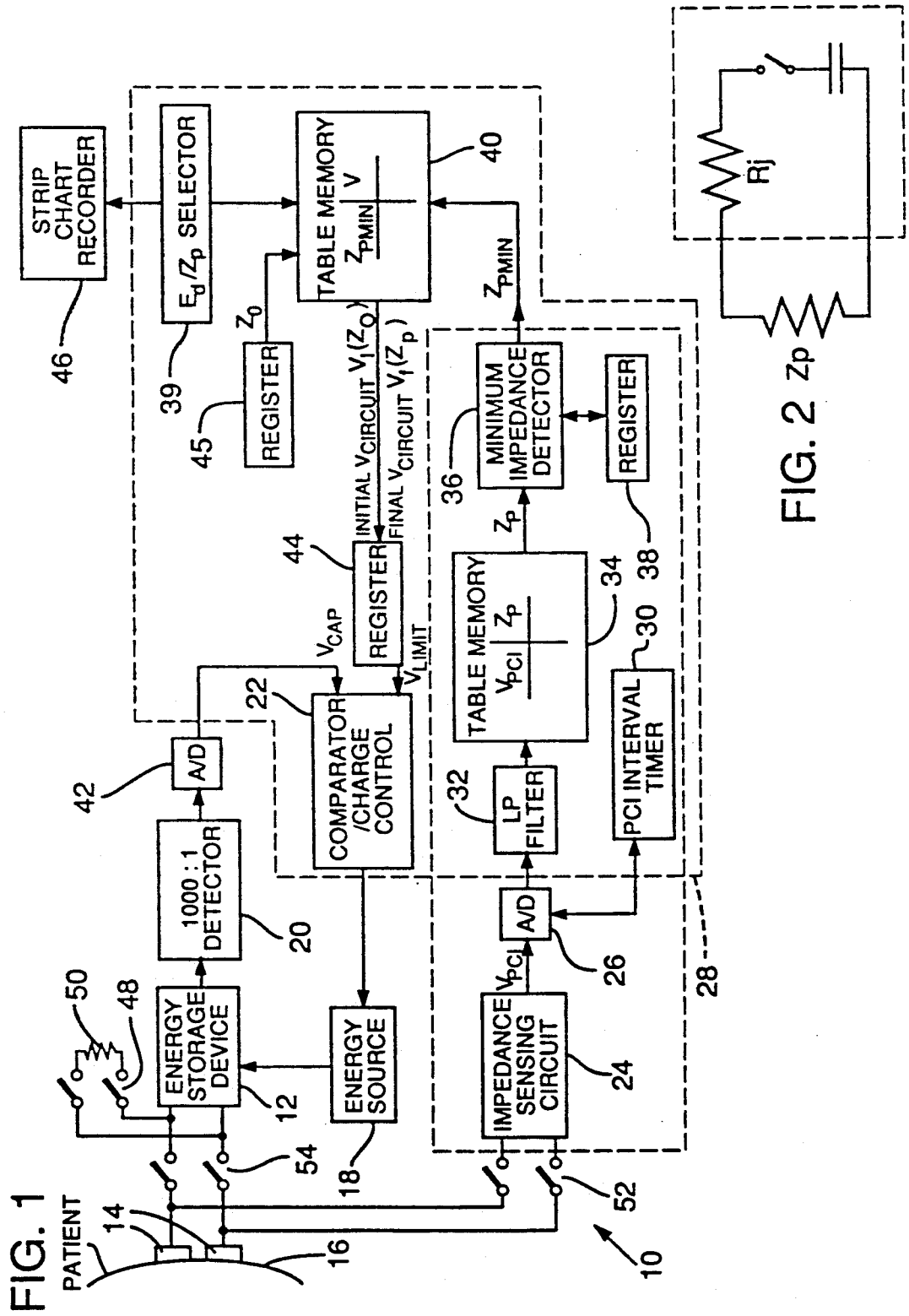

DEFIBRILLATION EMPLOYING AN IMPEDANCE-CORRECTED DELIVERED ENERGY

FIELD OF THE INVENTION

The present invention relates generally to the field of cardiac defibrillation, and in particular to a defibrillation method that optimizes the probability of successful and safe defibrillation on the first attempt.

BACKGROUND AND SUMMARY OF THE INVENTION

A defibrillator is a device used to administer a high intensity electrical shock through a pair of electrodes, or "paddles," to the chest of a patient in cardiac arrest. A selected, discrete quantity of energy is typically stored in a capacitor and is then electrically discharged into the patient through the paddle circuit.

Defibrillation is not a procedure with a certain and successful outcome. Rather, the probability of successful defibrillation depends on the condition of the patient and on the defibrillation discharge parameters. In order to practice defibrillation successfully and safely, it is important to quickly make an optimum choice of the defibrillation discharge intensity level. If the selected discharge intensity level is too low, defibrillation will not be successful and must be repeated at a higher intensity level until the patient is defibrillated. However, repeated defibrillation discharges at increasing intensity levels are more likely to cause damage to the heart. Also repeated discharges cause the patient to remain in ventricular fibrillation for a longer time. This causes the patient's condition to deteriorate, as metabolic imbalance and hypoxia develop, which, in turn, make the patient harder to defibrillate and reduce the prospect of successful recovery. One must, therefore, attempt to defibrillate as quickly as possible, and one must not initially attempt defibrillation at too low a discharge intensity.

On the other hand, it is well known that the probability of successful defibrillation increases, maximizes, and then decreases as the discharge intensity is steadily increased. (c.f. J. C. Schuder et al., "Transthoracic Ventricular Defibrillation," IEEE Transactions on Biomedical Engineering, Vol. BME-27, pp. 37-43, 1980.) Hence, one must also avoid excessive intensity levels. Excessive intensity levels not only reduce the probability of successful defibrillation, but also increase the risk of damaging the heart (myocardium and nerve system) as a result of an excessive discharge current flowing through the heart.

Due to these countervailing considerations, there have been a number of attempts to determine the effect of various discharge parameters on the efficacy and safety of defibrillation in order to help defibrillation operators choose the optimum intensity level for defibrillation.

(It should be noted that the general term "intensity" has been purposely used here to describe the level of the discharge. Intensity may be measured by any one of several discharge parameters such as energy stored in the defibrillator, energy delivered to the patient, peak or average current flowing through the patient, electrical charge or integrated electron flow through the patient, etc.)

In the following discussion, the defibrillation parameters which have been commonly used in the past are reviewed, with their corresponding limitations and inadequacies. The next discussion then identifies a new parameter which has not been used or discussed in the literature, but which appears to be the most general and accurate parameter which the operator can select and control in order to optimize the probability of successful and safe defibrillation on the first attempt.

Traditionally, defibrillators have been designed to allow control and selection of the energy $E_s$ stored in the defibrillator capacitor. This is equivalent to selection of the energy $E_d(50)$ which will be delivered into a 50 ohm load, i.e., delivered into the patient if a patient transthoracic impedance ($Z_p$) of 50 ohms is assumed. In fact, all defibrillator currently on the market are designed to permit the operator to select $E_d(50)$ only. Partly for that reason, generally accepted protocols for defibrillation, such as that published by the American Heart Association in the Journal of the American Medical Association ("Standards and Guidelines for Cardiopulmonary Resuscitation and Energy Cardiac Care," JAMA, Vol. 255, No. 21 pp. 2841-3044, Jun. 6, 1986) recommend that defibrillation be performed at an $E_d(50)$ of 200 Joules for the first two attempts (for adults in ventricular fibrillation) then at 300 or 360 Joules for subsequent attempts if required.

Unfortunately, the ability to select $E_d(50)$ does not optimize the probability of safe and successful defibrillation. This is due in large part to the fact that the patient's $Z_p$ is generally not known prior to discharge, and it is well known that $Z_p$ varies widely from patient to patient (from 15 to 140 ohms, with a mean of approximately 65 ohms, as reported in Kerber et al., "Transthoracic Resistance in Human Defibrillation, Influence of Body Weight, Chest Size, Serial Shocks, Paddle Size and Paddle Contact Pressure," Circulation, Vol. 63, No. 3, March 1981). The energy actually delivered to the patient depends on the value of $Z_p$ and will be markedly different from the intended energy $E_d(50)$ if the patient $Z_p$ is either much lower or much higher than 50 ohms.

Delivered energy is not a satisfactory parameter to control defibrillator success and safety, since both the energy required for defibrillation success and the energy threshold for damage to the heart depend strongly on the patient's $Z_p$. That is, a patient with a very low $Z_p$ (e.g., 25 ohms) may be successfully defibrillated by an energy of only 50 Joules and may suffer heart damage from an energy as low as 200 Joules, whereas a patient with a high $Z_p$ (e.g., 100 ohms) may require 300 Joules for successful defibrillation and may suffer damage only at much higher energies, e.g., 500 Joules or more.

Since the drawbacks of the selected energy approach have been recognized, there have been searches for better control parameters.

Generally accepted studies indicate that the basic processes of defibrillation and myocardial damage are more closely related to the flow of electrons through the heart than to the energy of the discharge. For example, Dr. Kerber in 1984 investigated the threshold for successful defibrillation in a patient population divided into two groups according to their $Z_p$. (Kerber et al., "Advance Prediction of Transthoracic Impedance in Human Defibrillation and Cardioversion: Importance of Impedance in Determining the Success of Low-Energy Shocks," Vol. 70, No. 2, August 1984.) The low-to-average $Z_p$ group had an average defibrillation threshold of 135 Joules (delivered energy) and 29 amperes (peak current), whereas the high $Z_p$ group had an average threshold of 211 Joules and 28 amperes. Hence, the defibrillation threshold measured by the peak current was the same for all patients irrespective of $Z_p$, whereas the defibrillation threshold measured by the delivered energy did increase with $Z_p$. These findings were supported by two later studies (Kerber et al., "Energy, Current and Success in Defibrillation and Cardioversion: Clinical Studies Using an Automated Impedance-Based Method of Energy Adjustment," Circulation, Vol. 77, No. 5, May 1988; and Lerman et al., "Current-Based Versus Energy-based Ventricular Defibrillation: A Prospective Study," American College of Cardiology, Vol. 12, No. 5, pp. 1259-64, November 1988). These studies led to a proposal that peak current $I_m$ be used, rather than energy $E_d$, as the control parameter selected for defibrillation.

Although peak current $I_m$ is a better choice than energy $E_d$, it still suffers from serious limitations, since the appropriate value of $I_m$ which yields a high probability of defibrillation success (while minimizing the risk of damage to the heart) depends strongly on the defibrillator discharge waveform.

For instance, in a study of defibrillation using trapezoidal waveforms of low or high tilt, Bourland showed that, for a given pulse duration d, high tilt waveforms required a much higher peak current $I_m$ than low tilt waveforms for successful defibrillation, while the average current $I_a$ was essentially the same for all values of tilt from 0 to 90%. (Bourland et al., "Strength-Duration Curves for Trapezoidal Waveforms of Various Tilts for Transchest Defibrillation in Animals," Medical Instrumentation, Vol. 12, No. 1, pp. 38-41, 1978.) Bourland then extended his study to another class of defibrillation discharge waveforms, i.e., the damped sinusoidal waveforms (DSW) which are used in almost all defibrillators currently on the market. Again, he found that the peak current varied markedly but, for a given duration of discharge, the average current $I_a$ required for successful defibrillation was essentially the same for all waveforms considered, i.e., DSW and trapezoidal with varying tilt. (Bourland et al., "Comparative Efficacy of Damped Sine Wave and Square Wave Current for Trans-chest Ventricular Defibrillation in Animals," Medical Instrumentation, vol. 12, no. 1, pp 42-45, 1978.) For a given pulse duration d, it appears that the peak current $I_m$ required for successful defibrillation varies widely with waveform, but the average current $I_a$ or, more accurately, the integrated electron flow or charge, is a more general parameter controlling the success of defibrillation.

However, one more generalization is needed to identify a parameter with universal validity, i.e., a parameter fairly independent of pulse duration, since it is known that various defibrillators currently on the market use circuit components (capacitors and inductors) which result in different discharge durations (generally in the 2 to 8 millisecond range for damped sinusoidal waveforms, but up to 15 or 20 milliseconds for certain trapezoidal waveform defibrillations).

It is well known that the discharge parameters (peak or average current, charge, energy) required for successful defibrillation vary with pulse duration. The laws of tissue stimulation were characterized at the turn of this century and can be expressed by the following equations:

$$I_a = b + \frac{k}{d}.$$

-continued
$$Q = I_a \cdot d = bd + k$$
$$E_d = RI_a^2 d = RI_aQ = R(k^2/d + 2bk + b^2d)$$

where d is the pulse duration, and t and k are constants characteristic of tissue. These relationships are represented graphically by the familiar strength-duration curves (Geddes et al., "Fundamental Criteria Underlying the Efficacy and Safety of Defibrillating Current Waveforms," Medical and Biological Engineering and Computing, Vol. 23, pp. 122-130, 1985).

A number of studies of internal and external defibrillation using a wide variety of waveforms have shown that the defibrillation threshold parameters follow the above-noted relationships fairly well, with b and k such that the minimum energy defibrillation occurs at a pulse duration of 3 to 5 milliseconds. Over the range of pulse duration most commonly (and justifiably) used for clinical defibrillation, i.e., 2 to 8 milliseconds, average current $I_a$ decreases as d increases, Q increases with d, but the product $I_a \cdot Q$, i.e., the ratio of discharge energy to patient transthoracic impedance, is essentially constant.

The foregoing discussion serves as introduction to our conclusion that there is a parameter which can be used as a predictor of successful defibrillation, so that a certain chosen value of this parameter can be associated with a given desired probability of successful defibrillation. This parameter value is universal in that it is essentially independent of patient transthoracic impedance and of discharge pulse waveform morphology and duration (whereas the optimum value of $I_a$ or Q depend on pulse duration, that of $I_m$ depends on both waveform morphology and pulse duration, and that of delivered energy depends on patient $Z_p$). This universal parameter is the impedance-corrected delivered energy $E_d/Z_p$ in Joules per ohm.

Using data collected in a recent experimental study of human defibrillation (Kerber et al., Circulation, Vol. 77, No. 5, May 1988, supra) and in a subsequent ongoing multicenter study coordinated by Kerber and not yet published, it can be confirmed that the probability of successful defibrillation is closely correlated to $E_d/Z_p$ for the various malignant arrhythmias (ventricular fibrillation, atrial fibrillation, atrial flutter, monomorphic or polymorphic ventricular tachycardia) which are commonly treated by defibrillation or by synchronized cardioversion. In the most important case, i.e., that of ventricular fibrillation, FIG. 5 shows the observed defibrillation success rate as a function of $E_d/Z_p$ for the current multicenter study. A minimum value $E_d/Z_p$ of approximately 3 Joules per ohm is required to achieve a high probability (70%) of successful defibrillation. The highest success probability (87%) is achieved for values of $E_d/Z_p$ in the range of 3.75 to 4.50.

The standard (energy based) defibrillation protocol published by the American Heart Association and the American Medical Association recommends the following sequence:
First attempt at 200 Joules;
Second attempt at 200 Joules; and
If unsuccessful, increase the energy to 300 or 360 Joules for subsequent attempts.

For reasons discussed earlier, this protocol has limited efficacy because patient $Z_p$ is highly variable and recommended initial level of 200 Joules is too low for patients with high $Z_p$ (e.g., 100 ohms) and is excessive (i.e., unnecessary risk of heart damage) for patients with low $Z_p$ (e.g., 25 ohms). According to the present invention, a defibrillation protocol based on the parameter $E_d/Z_p$ is proposed. An exemplary methodology is as follows:

First defibrillation attempt at 3 Joules per ohm;
Second defibrillation attempt at 3 Joules per ohm; and
If unsuccessful, increase the defibrillator output to 4.5 Joules per ohm for subsequent attempts.

An alternate, more aggressive protocol would be to select a $E_d/Z_p$ value of 4 for initial defibrillation The foregoing and additional advantages of the present invention will be more readily apparent from the owing detailed description thereof, which proceeds with reference to the accompanying drawings.

BRIEF DESCRIPTION OF THE DRAWINGS

FIG. 1 is a schematic block diagram of a defibrillator apparatus with which the method of the present invention may be practiced.

FIG. 2 is an equivalent circuit representation representing the load into which a dafibrillator capacitor discharges.

DETAILED DESCRIPTION

Figure 3A:
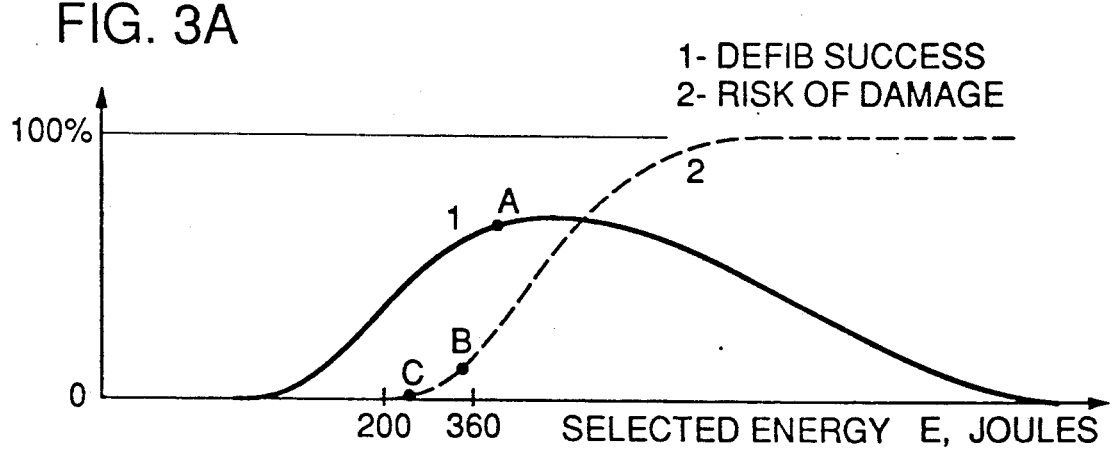
FIGS. 3A-3C show a set of probability curves illustrating percentages of successful defibrillation and probability of damage to the myocardium as functions of selected energy, selected current, and selected impedance-normalized delivered energy.

As noted, the present invention is an improved defibrillation methodology. The apparatus used to practice the invention is similar to that employed with prior art defibrillation techniques, such as impedance-based current defibrillation. Such apparatuses are shown, inter alia, in U.S. Pat. Nos. 4,840,177, 4,771,781 and 4,574,810, the disclosures of which are incorporated herein by reference. For expository convenience, the present invention is illustrated with reference to an apparatus 10 similar to that shown in U.S. Pat. 4,771,781, with some differences noted in the following description.

Referring to FIG. 1, the defibrillation apparatus 10 includes an energy storage device 12, such as a capacitor, paddles 14 for applying an electrical shock from the capacitor to a patient 16, and a power supply 18 for charging the capacitor device. A detector 20 detects the charge accumulated by the capacitor and feeds this data back to a comparator/charge control circuit 22, which controls the capacitor's charging accordingly. Charging of the capacitor continues until the voltage across the capacitor reaches a target value, detailed below.

The defibrillator 10 also includes an impedance measurement system 24 that excites the patient 16 with a low current A.C. excitation signal through paddles 14 and produces a corresponding analog output signal inversely proportional to the patient's transthoracic impedance. In the preferred embodiment, the excitation signal has a frequency of 31 kilohertz, a frequency at which the patient's transthoracic impedance has been found to approximate the patient's impedance to a defibrillation pulse. In alternate embodiments, however, other excitation frequencies may be used.

The output signal from the impedance measurement system 24 is provided to an eight bit analog-to-digital converter 26, such as a National Semiconductor type ADC-0844, which periodically samples the analog signal and converts each sample into digital form. The frequency at which the A/D converter 26 samples is dictated by an associated single board computer 28 and is approximately 240 hertz in an illustrative embodiment. (Computer 28 may be built around an Intel 8052 microprocessor with associated ROM and is used to implement many of the subsequent processing functions illustrated in FIG. 1.) The A/D sampling continues during a predetermined measurement period, here termed the patient contact interval (PCI), the length of which is set by a software implemented decrementing timer 30 in the computer 28. This period may be approximately one second, a period long enough to yield approximately 240 impedance samples.

The samples output from the A/D converter 26 are provided to the single board computer 28 for further processing. The first processing step is to low pass filter the digitized voltage using a software implemented filter 32 to remove noise that may be impressed on this signal. The filtered, digitized voltage signal is then used to index a first look-up table 34 that correlates the output from the A/D converter 26 to a value of patient transthoracic impedance. The first look-up table 34, together with a second look-up table 40 illustrated in FIG. 1, are implemented using the ROM memory associated with the single board computer 28.

Each transthoracic impedance value retrieved from the first look-up table 34 is compared by a minimum impedance detector 36 against a minimum impedance value $Z_{min}$ stored in a register 38 in the microprocessor. This register is initially loaded with a value of 255 ohms (FF hex). Thereafter, as each of the impedance values is retrieved from the look-up table 34, it is compared with the register value. If a sampled impedance value is lower than the previously stored minimum, the register is loaded with the new minimum value. At the end of the one second PCI interval, this $Z_{min}$ register contains the lowest impedance value sampled during the interval. This value, here termed $Z_p$, is the patient's transthoracic impedance.

At the conclusion of the one second sampling interval, the $Z_p$ value is used as a first index into a second look-up table memory 40. The desired impedance-normalized delivery energy $(E_d/Z_p)$ is used as a second index into the table. This latter figure is typically provided from the computer 28 according to a predefined protocol. (In the illustrated embodiment, this protocol specifies a figure of 3 Joules/Ohm for the first and second successive defibrillation attempts, and a figure of 5 Joules/Ohm for the third and successive attempts.) Alternatively, the impedance-normalized delivered energy may be selected by the operator using a switch 39 on the front panel of the defibrillator. The output from the second look-up table 40 in response to these two inputs is the voltage V to which the capacitor should be charged to deliver the desired value of $E_d/Z_p$. This target voltage value V is stored in a register 44 associated with the computer 28.

FIG. 2 shows a simplified equivalent patient/defibrillator circuit with which operation of the second look-up table 40 may be more readily understood. It will be recognized that the defibrillator capacitor 12 discharges into a series circuit composed of the patients's transthoracic impedance $Z_p$ and a defibrillator internal resistance $R_j$ (this latter resistance is associated with a series inductor, rot shown). When discharged, the energy E stored in the capacitor distributes proportionately between these resistive elements in accordance with their relative values. The energy delivered to the patient can thus be represented as:

$$E_d = E_s Z_p / (Z_p - R_i) \quad (1)$$

If an impedance-normalized delivered energy ($E_d/Z_p$) of 3 Joules/Ohm is desired, the total delivered energy $E_d$ is simply $3Z_p$ Joules. Solving equation (1) for the capacitor charge necessary to deliver this energy yields:

$$E_s = 3Z_p(Z_p - R_i)/Z_p - R_i) \quad (2)$$

Capacitor charge $E_s$ is related to capacitor voltage V by the formula:

$$E_s = \tfrac{1}{2}cV^2 \quad (3)$$

Solving equation (3) for the voltage necessary on the capacitor 12 to yield the desired impedance-normalized delivered energy to the subject patient yields:

$$V = SQRT(2 \cdot 3(Z_p - R_i)/C) \quad (4)$$

In this equation, the values $R_i$ and C are invariant and depend on the defibrillator's particular design. $R_i$ is typically in the range or 9 to 13 ohms for most defibrillators. C is typically in the range of 30 to 60 microfarads. The two variables are the patient impedance $Z_p$ and desired impedance-normalized delivered energy (3 Joules/Ohm in this example). The second look-up table 40 is organized as a two-dimensional array indexed by these two variables and contains the corresponding results of equation (4), indicated by $V_{CIRCUIT}$ in FIG. 1.

Returning to FIG. 1, the capacitor 12 is charged by the power supply 18 to the voltage $V_{CIRCUIT}$ (also referenced herein as the "limit" or "target" voltage) obtained from the second look-up table 40. The power supply 18 can comprise a conventional flyback charger in which a 14 volt DC battery is applied to one end of a transformer winding and the bottom end of that winding gates on and off to ground. Suitable chargers are described in U.S. Pat. Nos. 4,233,659 and 4,119,903.

The voltage on the capacitor 12 is sampled through a 1000 to 1 voltage divider network 20 and is converted into digital form by a second analog-to-digital converter 42. (The second ADC 42 is actually a second channel of the National Semiconductor ADC 0844 employed as the first ADC 26.) The output from the second ADC 42 is compared by the computer with the target voltage V stored in the register 41. The computer 28 allows the power supply 18 to continue charging the capacitor until this target voltage is reached.

Once charged to the desired level, the defibrillator charge is discharged into the patient by known techniques.

To expedite charging of storage capacitor 12, it is generally desirable to begin the charging operation before the patient's transthoracic impedance, and consequently the final limit voltage, have been determined. To accomplish this, the patient is assumed to have an arbitrary transthoracic impedance $Z_o$ and charging is initiated toward the initial voltage limit $V_I$ which corresponds to the selected $E_d/Z_o$, according to equation 4. This value $V_I$ comes from the look-up table 40 and is stored in register 44, for input into comparator 22. Any reasonable value of $Z_o$, e.g., 50 or 70 ohms, could be assumed for this purpose. When the actual patient impedance $Z_p$ has been determined, the corresponding capacitor voltage is obtained from look-up table 40 and the capacitor charge is increased or decreased to achieve the desired voltage $V_f$.

This process can be modified to accommodate the common practice of defibrillator operators who often will initiate charge, delay placing the paddles firmly on the patient until the charge is complete or nearly complete, then expect to discharge very quickly. Since patient impedance can be measured only when the paddles are in contact with a patient, the desired capacitor voltage can only be known after the paddles are on the patient, and it is desirable to reach this voltage very quickly (a fraction of a second) after the paddles are placed on the patient. Due to inherent limitations in the power supply, the capacitor voltage can be increased only slowly, whereas it can be *decreased* very rapidly by partial discharge into an internal resistive load. Hence, quick adjustment to the desired capacitor voltage can only be accomplished by assuming a very high value of patient impedance (hence a high initial voltage limit) when initiating the charge, so that the rapid adjustment to the desired voltage is always a reduction of the capacitor voltage. A specific $Z_o$ value of 150 ohms is proposed in the preferred embodiment and is stored in a register 45. Hence, charging is initiated toward the initial voltage limit $V_I$ which is the smaller of the voltage $V_o$ which corresponds to the selected $E_d/Z_p$ value and an impedance of 150 ohms, or the voltage $V_I$ which yields the maximum delivered energy $E_{max} = 360$ Joules. When this method is used, the defibrillation procedure can be summarized as follows:

1) Charge the capacitor to the smaller of 360 Joules or the value corresponding to the desired $E_d/Z_p$ with $Z_p = 150$ ohms;
2) Place paddles firmly on patient;
3) Just prior to discharge, measure actual patient impedance $Z_p$ (less than 150 ohms) and reduce capacitor charge to the correct value by partial internal discharge; and
4) Discharge into patient.

This feature may be used in all defibrillation protocols which require determination of $Z_p$ to set the desired discharge level. Examples of such protocols are current based defibrillation (as disclosed in U.S. Pat. Nos. 4,840,177 and 4,771,781) and the impedance-based defibrillation discussed here.

Figure 3B:
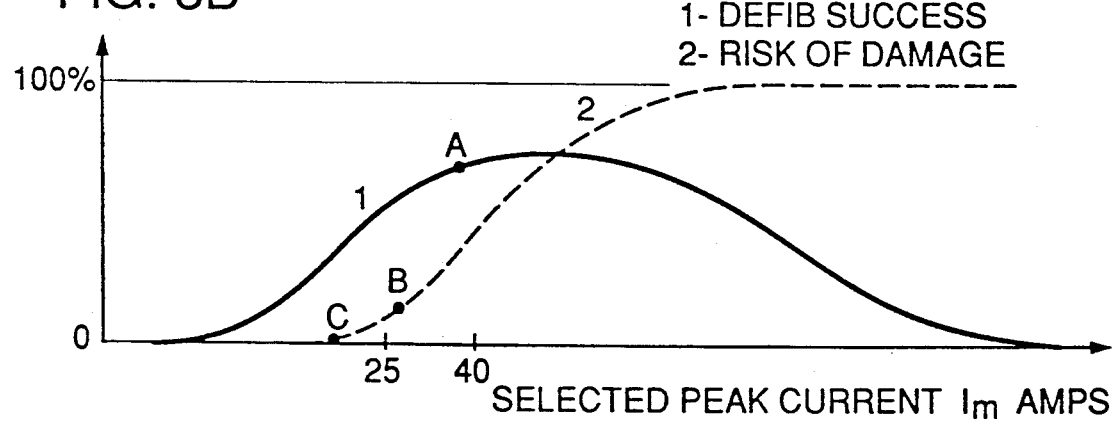
Figure 3C:
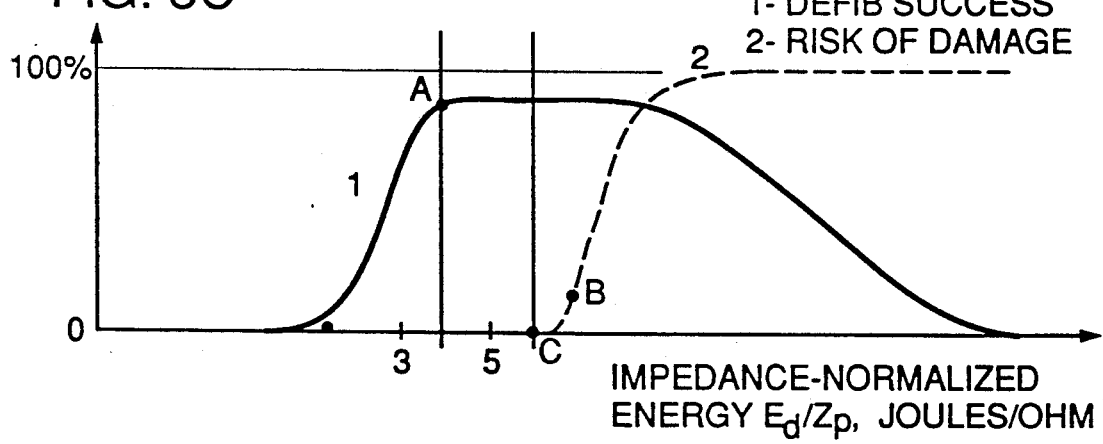

The impedance-normalized delivered energy parameter on which the present methodology is based provides significant advantages over prior art approaches. These advantages are illustrated in FIGS. 3A-3C, which represent curves plotting probability of defibrillation success and of damage to the myocardium as a function of selected energy, selected current and selected impedance-normalized delivered energy, respectively. The curves for selected energy (FIG. 3A) are supported by a great deal of published data and are widely known and accepted in their general form. The curves for selected current (FIG. 3B) are supported by a smaller amount of published data but are known and accepted by medical practitioners expert in defibrillation. The curves for impedance-normalized energy (FIG. 3C) are not generally known since this parameter has not been discussed or used previously and is indeed one of the objects of this intention. In all three cases the precise curves are not exactly known and in fact differ somewhat among various studies. However, the general form of the curves is accepted and suffices to demonstrate the advantages of impedance-normalized energy selection mode.

The curves shown in FIG. 3A represent the selected energy approach. This technique is the one currently recommended by the American Heart Association and specifies that defibrillation first be attempted with an energy of 200 Joules, followed by a second attempt at 200 Joules and further attempts at 300-360 Joules. The approximate position of these energy values is illustrated in FIG. 3A.

The wide spread in curve 1, and the correspondingly lower probability of success at its maximum, are due in large part to the variability in transthoracic impedance among the universe of possible patients. This variability is not taken into account in the selected energy approach, compromising the approach's efficacy for any given patient.

Furthermore, this wide spread of the two FIG. 3A curves (success and damage) results in an overlap therebetween. Hence, the energy required for a high defibrillation success (point A) is higher than the energy required for onset of damage (point C) or for an appreciable risk of damage (point B). Thus it appears impossible to specify an energy selection which is both highly successful and absolutely safe for all patients.

The curves shown in FIG. 3B represent the selected current approach. This is the technique adopted in systems according to U.S. Pat. No. 4,840,177 and involves measuring the patient's transthoracic impedance and charging the defibrillator capacitor to the level required to induce a desired current to flow through the patient on discharge.

The wide spread in this curve 1, and the correspondingly lower probability at its maximum, are due to variability in the defibrillation pulse shape and duration among the universe of defibrillator designs. For example, a defibrillation pulse with a duration of 2 milliseconds will have a markedly different effect than a defibrillation pulse with a duration of 8 milliseconds, even if both supply a current of 30 amperes to the patient. This variability is not taken into account in the selected current approach, rendering it unsuitable as a universal standard that may be applied to all defibrillator designs.

The adverse consequence of this variability is again to cause a sufficiently wide spread in the two curves (success and damage) that significant overlap exists (i.e., point A corresponds to a larger current than points B and C). Hence, no single value of selected current is both highly successful and fully safe for all defibrillators in use. For a given defibrillator, an appropriate value of selected current specific to that defibrillator which is both highly successful and fully safe may exist; however, this value will be different for different defibrillator models.

The curves shown in FIG. 3C represent the approach adopted by the present invention: impedance-normalized delivered energy. As will be noted, the defibrillation success curve has a steeper rise and higher maximum value than in FIGS. 3A and 3B. The reason behind this optimized response is that transthoracic impedance and discharge waveform are not left as variables. The patient transthoracic impedance is measured and the capacitor charge is set accordingly. Similarly, the waveform shape and duration are not factors because energy is used as the relevant parameter instead of current. That is, whether a defibrillator has a 2 millisecond discharge pulse or a 8 millisecond discharge pulse doesn't matter because for a given patient the delivered energy will be the same. (This same delivered energy will be manifested as currents of different magnitude in roughly inverse proportion to the discharge durations.)

It is also apparent in FIG. 3C that the damage curve has a steeper rise than in FIGS. 3A and 3B, for the same reasons just discussed. The most important consequence of this is that overlap between the success and damage curves is minimized in FIG. 3C, i.e., the minimum $E_d/Z_p$ for high defibrillator success probability (point A) is now smaller than the values corresponding to onset of damage (point C) and significant risk of damage (point B). Hence it is now possible to choose a universal value of impedance-normalized energy which is both highly successful and fully safe.

Figure 4A:
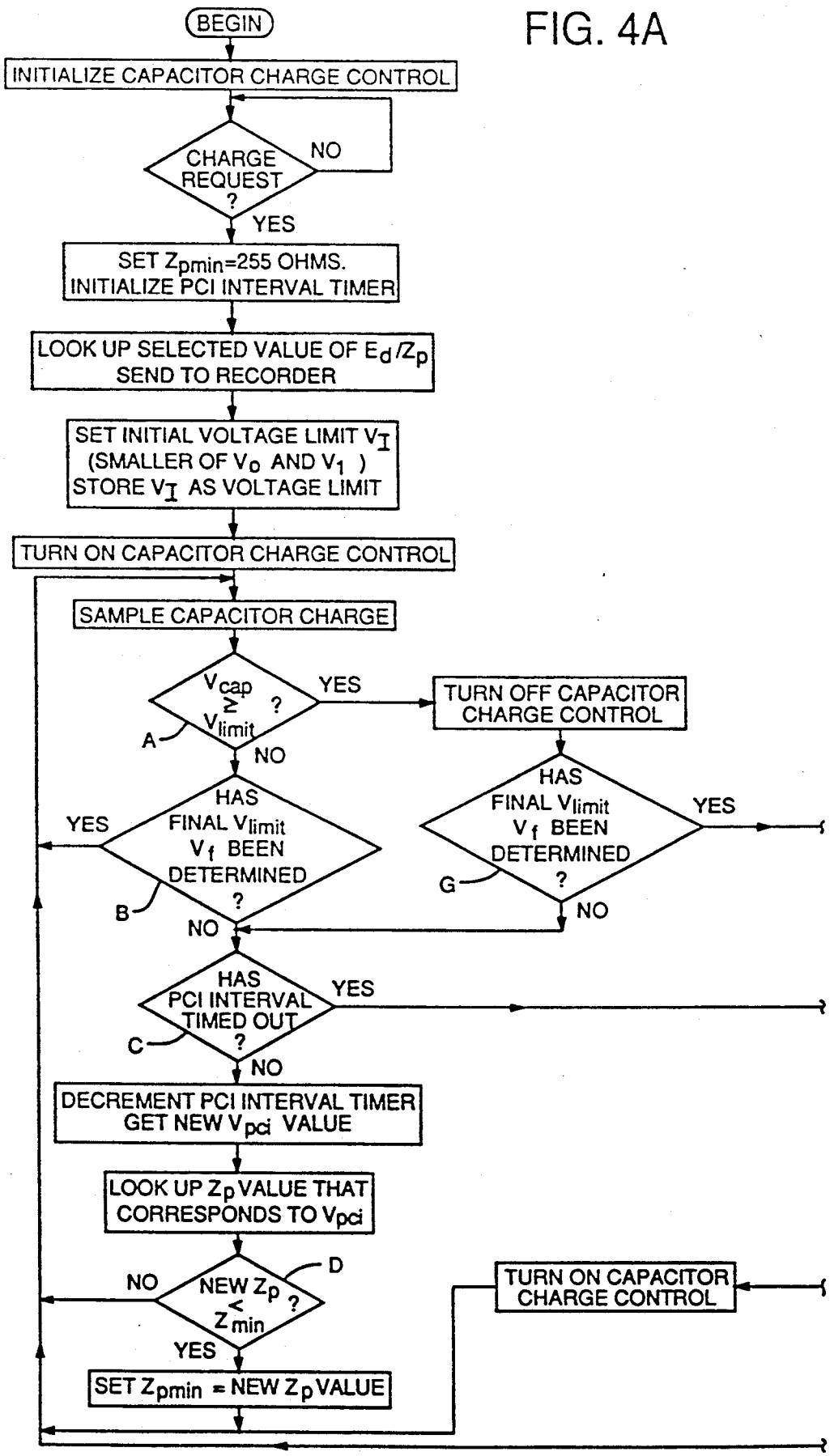
FIGS. 4A and 4B show a flow chart diagram of the defibrillator operation.
Figure 4B:
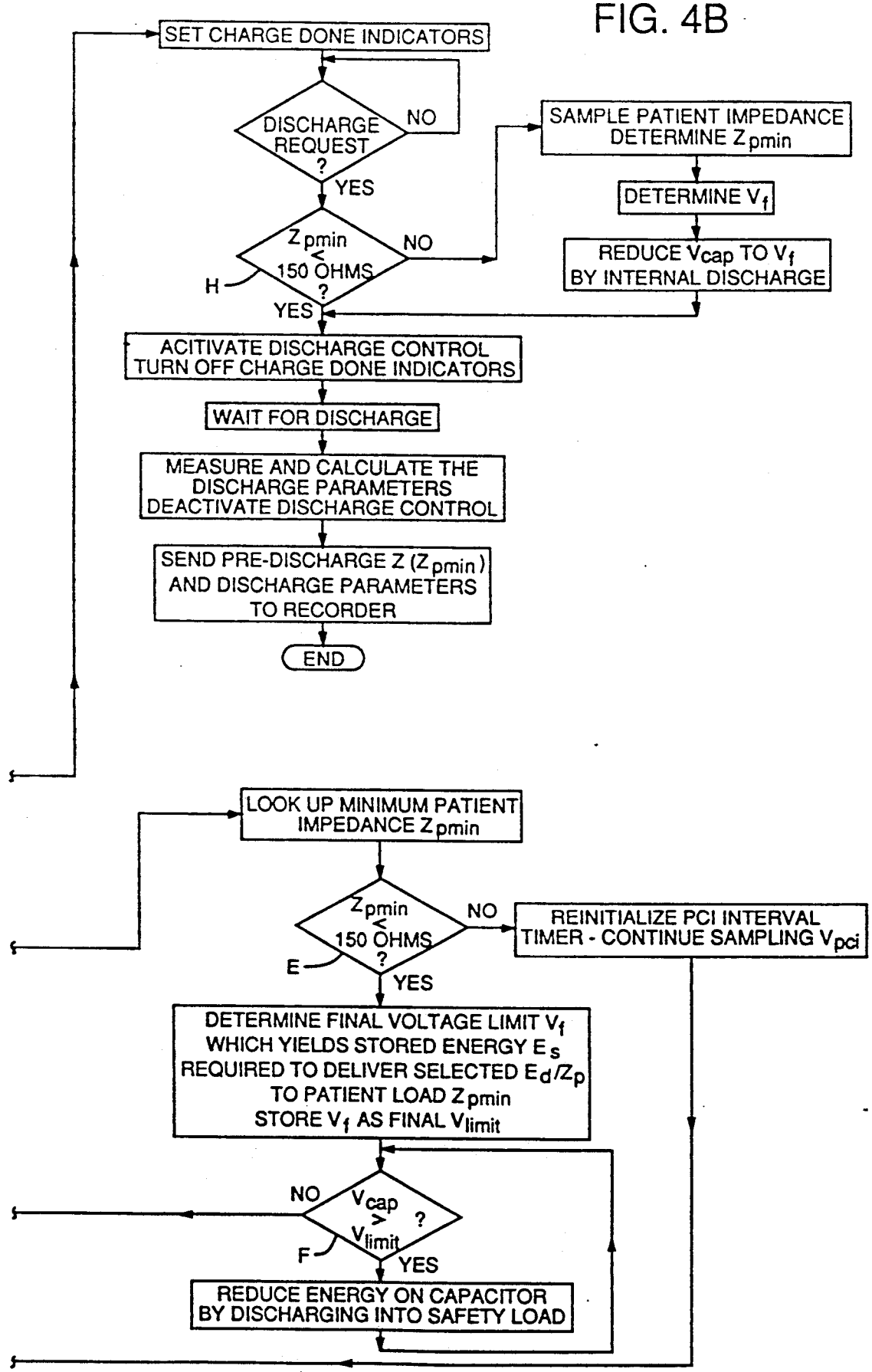
Figure 5:
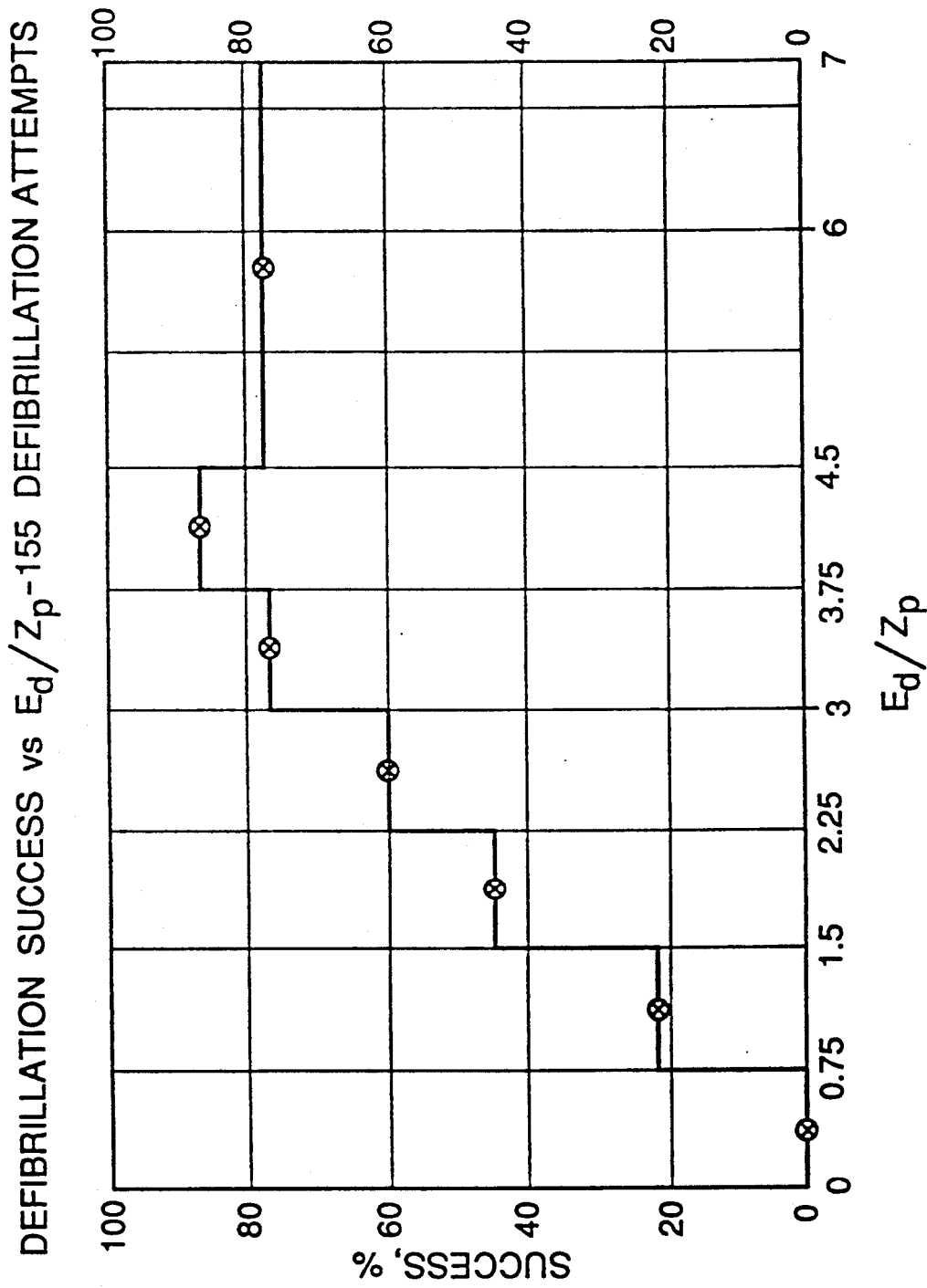
FIG. 5 is a graph of defibrillation success vs. impedance-corrected delivered energy.

FIG. 4 is a flow chart detailing the various sequences of steps executed by the above-described embodiment of the present invention.

When the instrument is activated, capacitor charge control 22 and voltage limit register 44 are reset, resetting the capacitor limit voltage stored in voltage limit register 44 to zero. When selection switch 39 is operated to initiate circuit operation, an initial $Z_{pmin}$ value of 255 ohms is loaded in minimum impedance register 38 and PCI contact interval timer 3( is initialized to a one second time period. The desired value of $E_d/Z_p$ selected on switch 39 is sent to strip chart recorder 46 for display. The initial voltage limit $V_I$ corresponding to the selected $E_d/Z_o$ (with $Z_o=150$ ohms) second look-up table 40 and is stored in voltage limit register 44. If the capacitor voltage $V_{cap}$ is less than this limit $V_I$ (decision block A), the process proceeds to block B to check whether the final voltage limit has yet been determined. If it has not, the process proceeds to block C to examine whether the one second PCI interval has yet expired. If it has not, PCI interval timer 30 is decremented and a new transthoracic impedance sample is taken. The resultant impedance value provided by first look-up table 34 is compared against the previously stored minimum impedance value $Z_{pmin}$ in block D. If it is less than the previously stored minimum value, the old minimum value is replaced by the new value and the processing loop repeats, comparing the capacitor voltage with the limit voltage.

The above-described loop repeats itself at a rate of approximately 240 hertz until the one second PCI timer 30 has timed out. The lowest impedance value $Z_{pmin}$ sampled during the one second interval is compared to $Z_o=150$ ohms in block E and a fundamental branching occurs. If $Z_{pmin}<150$ ohms, one assumes that the patient minimum impedance $Z_p$ has been properly measured. $Z_{pmin}$ is entered into second look-up table 40 which determines the final limit voltage $V_f$. This final limit voltage is substituted in voltage limit register 44 which previously contained the initial limit voltage.

The process then checks, iu block F, whether the voltage on capacitor 12 is greater than the final limit voltage which has just been determined. If so, the capacitor is connected through relay contacts 48 to discharge load 50 to bleed off the excess charge quickly. When the charge bleeds down to the desired final voltage, the process returns to block A.

At block A, the voltage on the capacitor is again examined. This time through the loop, the final voltage limit has been determined, so block B causes the process to loop indefinitely, comparing the voltage on the capacitor with the final limit voltage until the limit voltage is reached. At this point, charging of capacitor 12 is discontinued.

It may happen that the voltage limit initially stored in voltage limit register 44 is reached before the final voltage limit has been determined. In this case, charging is interrupted and the process loops idly through block G until the final voltage limit is determined. If, after the final voltage limit is determined, it is found at block A to be greater than the initial voltage limit which has already been reached, charging will resume until the new final voltage limit is reached.

If, in block E, $Z_{pmin}$ is greater than 150 ohms, one assumes that the patient impedance has not been properly measured, possibly because the paddles were not applied to the patient. The PCI interval timer is reinitialized and the sequence of operations in blocks A through G is resumed.

After the charge on the capacitor has reached the final voltage limit, the process escapes from the charging loop at block G. The apparatus then sets a ready indicator and awaits a discharge request. If any charge is lost from the capacitor due to the capacitor's internal leakage resistance while awaiting a discharge request, a trickle charge circuit (not shown) restores the lost charge.

When a discharge request is received, $Z_{pmin}$ is again compared to $Z_o = 150$ ohms (block H). If $Z_{pmin} < 150$ ohms, relay contacts 52 open and relay contacts 54 close, discharging capacitor 12 through the patient. The peak instantaneous current actually delivered to the patient is detected by a current sampling loop (not shown) and the associated energy delivered, patient impedance and $E_d/Z_p$ are calculated using known techniques. These parameters are then sent to strip chart recorder 46 for display.

If $Z_{pmin} > 150$ ohms, one assumes that patient impedance was not properly measured, again presumably because paddles were not placed on the patient during the charge cycle. The PCI circuit is reactivated, an instantaneous (e.g. 10 msec) measurement of $Z_{pmin}$ is performed, the corresponding $V_f$ is determined, $V_{cap}$ is quickly reduced to $V_f$ by internal discharge, and patient discharge proceeds as before.

From the foregoing, it will be recognized that impedance-normalized delivered energy (in Joules per ohm) is a control parameter that can be used advantageously as a predictor of successful defibrillation. This parameter value is essentially independent of patient transthoracic impedance and of discharge pulse waveform (i.e. it has the same value for all patients and all defibrillators), a property not shared by any of the other control parameters which have heretofore been used or proposed. Impedance-normalized delivered energy is thus suitable as a standard on which a universal defibrillation protocol may be based.

Having described and illustrated the principles of this invention with reference to a preferred methodology and associated apparatus, it will be apparent that the invention can be modified in arrangement and detail without departing from such principles. For example, while the invention has been illustrated with reference to a defibrillator in which energy is stored in a capacitor, it will be recognized that in other embodiments, alternate energy storage devices, such as inductors, may be used. In such case, the parameters appropriate to an inductor (flux and current) are used in lieu of the charge and voltage parameters referenced in connection with the illustrated capacitive storage device.

In view of the wide variety of embodiments to which the principles of the present invention may be applied, it should be recognized that the detailed embodiment is illustrative only and should not be taken as limiting the scope of our invention. Rather, we claim as our invention all such modifications as may come within the scope and spirit of the following claims and equivalents thereto.

We claim:

1. A method of providing a defibrillation pulse to a patient to restore normal cardiac rhythm, the method comprising the steps:
    establishing a desired value of impedance-corrected delivered energy ($E_d/Z$);
    measuring a transthoracic impedance Z of the patient;
    determining the voltage to which a capacitor must be charged to provide the desired value of impedance-corrected delivered energy to a patient having the transthoracic impedance measured;
    providing charge to or from the capacitor until the calculated voltage is reached; and
    discharging the charged capacitor through the patient.

2. The method of claim 1 which includes charging the capacitor prior to measuring the transthoracic impedance of the patient, and subsequently dumping charge from the capacitor until the calculated voltage is reached.

3. The method of claim 1 which includes establishing a desired value of impedance-corrected delivered energy ($E_dZ$) without reference to particular characteristics of the patient.

4. The method of claim 3 which includes establishing a desired value of impedance-corrected delivered energy of 3 Joules/Ohm.

5. The method of claim 4 which further includes:
    repeating the charging and discharging steps if the patient's normal cardiac rhythm is not restored by the first discharge; and
    establishing a desired value of impedance-corrected delivered energy of approximately 5 Joules/Ohm in determining the voltage to which the capacitor is to be charged in the repeated charging step.

6. The method of claim 3 which further includes repeating the charging and discharging steps if the patient's normal cardiac rhythm is not restored by the first discharge.

7. The method of claim 6 in which the repeated charging step includes charging the capacitor to a higher voltage than the voltage initially determined.

8. In a defibrillation method that includes the steps of detecting a patient's transthoracic impedance, calculating an electrical charge that corresponds to the detected impedance according to a predetermined relationship, providing the calculated electrical charge to a storage capacitor, and discharging the charged capacitor through the patient, an improvement wherein the predetermined relationship on which the capacitor charge is based is a desired value of delivered energy per unit of patient transthoracic impedance, said value being predetermined irrespective of particular characteristics of the patient and irrespective of the shape of the waveform produced in discharging the capacitor.

9. A defibrillator for providing a defibrillation pulse to a patient to restore normal cardiac rhythm, comprising:
    a capacitor;
    means for establishing a desired value of impedance-corrected delivered energy ($E_dZ$);

means for measuring a transthoracic impedance Z of the patient;

means for determining the voltage to which the capacitor must be charged to provide the desired value of impedance-corrected delivered energy to a patient having the transthoracic impedance measured;

means for providing charge to or from the capacitor until the voltage thereacross equals the calculated voltage; and means for discharging the charged capacitor through the patient.

10. A method of providing a defibrillation pulse to a patient to restore normal cardiac rhythm, the method comprising the steps:

providing an energy storage device, the energy stored in said device being related by a formula to a physically measurable parameter;

establishing a desired value of impedance-corrected delivery energy ($E_d/Z$);

measuring a transthoracic impedance Z of the patient;

determining a first amount of energy, said first amount being the amount of energy to be delivered to the patient, said first amount being equal to the product of the impedance-corrected delivered energy and the patient's transthoracic impedance;

providing to the energy storage device a second amount of energy calculated to provide to the patient said first amount of energy; and transferring energy stored in the storage device to the patient.

11. The method of claim 10 which further includes providing to the energy storage device more than the second amount of energy and diminishing the energy stored therein down to the second amount prior to transferring energy stored therein to the patient.

12. The method of claim 11 which further includes providing to the energy storage device more than the second amount of energy prior to measuring the transthoracic impedance of the patient.

13. The method of claim 1( in which the second amount of energy is greater than the first amount of energy to account for energy lost between the storage device and the patient.

14. The method of claim 10 in which the providing step includes:

computing the value of the physically measurable parameter required to store in the energy storage device said second amount of energy;

measuring the energy storage device to ascertain the value of said parameter; and providing energy to or from the energy storage device until the measured parameter equals the computed parameter.

15. A defibrillation method comprising the steps:

detecting a patient's transthoracic impedance;

providing a corresponding, target level of energy to an energy storage device, said target level being selected in response to the detected transthoracic impedance so as to provide a desired impedance-corrected delivered energy to the patient upon discharge of the device through the patient;

said providing step including providing a second level of energy greater than said target level to the energy storage device; and removing energy from the storage device until the target level is reached.

* * * * *